(12) United States Patent
Watson et al.

(10) Patent No.: US 6,613,362 B2
(45) Date of Patent: Sep. 2, 2003

(54) HERBAL FORMULATION WHICH ACTS AS AN INTESTINAL BOWEL SOOTHER

(75) Inventors: Tommy Stanley Watson, Dunedin, FL (US); Brenda F. Watson, Dunedin, FL (US)

(73) Assignee: Renew Life Formulas, Inc., Clearwater, FL (US)

( * ) Notice: Subject to any disclaimer, the term of this patent is extended or adjusted under 35 U.S.C. 154(b) by 32 days.

(21) Appl. No.: 10/041,314

(22) Filed: Jan. 8, 2002

(65) Prior Publication Data

US 2003/0129260 A1 Jul. 10, 2003

(51) Int. Cl.[7] .......................... A61K 35/78; A61K 47/00
(52) U.S. Cl. .................. 424/732; 424/725; 424/736; 424/738; 424/747; 424/756; 424/757; 424/769; 424/771; 424/439; 514/867; 514/892
(58) Field of Search .................. 424/725, 439, 424/732, 736, 738, 747, 756, 757, 769, 771; 514/867, 892

(56) References Cited

U.S. PATENT DOCUMENTS 6,280,751 B1 * 8/2001 Fletcher et al.

* cited by examiner

Primary Examiner—Christopher R. Tate
(74) Attorney, Agent, or Firm—MacMillan, Sobanski & Todd; Donald R. Fraser

(57) ABSTRACT

An herbal formulation which acts as an intestinal bowel soother is disclosed which comprises: slippery elm bark; German chamomile flower; fenugreek seed; fennel seed; skullcap herb; cranberry fruit; peppermint leaf; a mixture of Chinese herbs, comprising atractylodes root, capillary artemisia herb, codonopsis root, Job's tears seed, schisandra fruit, agastache whole plant, Chinese licorice root, Chinese thoroughwax, ginger root, Korean ash branches bark, magnolia bark, phellodendron bark, poria cocos root, psyllium seed, Chinese goldthread, Chinese white peony root, costus root, silver root, tangerine peel, and angelica root; and methylsulfonylmethane.

33 Claims, No Drawings

HERBAL FORMULATION WHICH ACTS AS AN INTESTINAL BOWEL SOOTHER

FIELD OF THE INVENTION

The present invention relates generally to an herbal formulation. More particularly, the invention is directed to an herbal food supplement comprising a mixture of Western and Chinese herbs which can act as an intestinal bowel soother.

BACKGROUND OF THE INVENTION

Herbal formulations have been used as dietary supplements and natural medicaments for many years. Such formulations may aid the body in dealing with a number of intestinal maladies such as, for example, irritable bowel syndrome.

Irritable bowel syndrome is one of today's most frequently occurring gastrointestinal disorders, accounting for approximately 40% of all visits to gastroenterology practices. Sometimes called spastic colitis or nervous colon, common symptoms of irritable bowel syndrome may include cramping, bloating, and alternating diarrhea and constipation. People afflicted with irritable bowel syndrome have been shown to be almost three times more likely to miss work (13.4 days per year vs. 4.9 days per year) than those who do not suffer from this infirmity.

The exact cause for irritable bowel syndrome is not known. Conventional therapies include dietary changes and nutritional supplements. Significant changes in dietary habits and the elimination of common foods that are known to cause allergies (such as, for example, refined carbohydrates, dairy or lactose products, and sugars) may reduce irritable bowel syndrome symptoms.

It would be desirable to prepare an herbal formulation that would act as a food supplement and at the same time assist in relieving the symptoms of irritable bowel syndrome by soothing the intestinal bowels.

SUMMARY OF THE INVENTION

Accordant with the present invention, a beneficial herbal formulation has surprisingly been discovered. It comprises the following ingredients:
slippery elm bark;
German chamomile flower;
fenugreek seed;
fennel seed;
skullcap herb;
cranberry fruit;
peppermint leaf;
a mixture of Chinese herbs, comprising atractylodes root, capillary artemisia herb, codonopsis root, Job's tears seed, schisandra fruit, agastache whole plant, Chinese licorice root, Chinese thoroughwax, ginger root, Korean ash branches bark, magnolia bark, phellodendron bark, poria cocos root, psyllium seed, Chinese goldthread, Chinese white peony root, costus root, silver root, tangerine peel, and angelica root; and methylsulfonylmethane.

The herbal formulation according to the present invention is useful as a food supplement, and additionally may be particularly useful as an intestinal bowel soother for those who experience irritable bowel syndrome.

DETAILED DESCRIPTION OF THE PREFERRED EMBODIMENT

The present invention is directed to an herbal formulation useful as a food supplement and as an intestinal bowel soother, comprising: slippery elm bark; German chamomile flower; fenugreek seed; fennel seed; skullcap herb; cranberry fruit; peppermint leaf; a mixture of Chinese herbs, comprising atractylodes root, capillary artemisia herb, codonopsis root, Job's tears seed, schisandra fruit, agastache whole plant, Chinese licorice root, Chinese thoroughwax, ginger root, Korean ash branches bark, magnolia bark, phellodendron bark, poria cocos root, psyllium seed, Chinese goldthread, Chinese white peony root, costus root, silver root, tangerine peel, and angelica root; and methylsulfonylmethane.

Slippery elm bark (*ulmus rubra*) is a well-known herb used to counteract inflammation and relieve gastro-intestinal irritation. Slippery elm bark may be present in the inventive formulation at a concentration ranging from about 5 to about 20 weight percent. Preferably, the concentration of slippery elm bark is about 12.5 weight percent.

German chamomile flower (*matricaria recutita*) is a well-known herb which acts as an anti-inflammatory, anti-bacterial, and anti-allergenic agent. German chamomile flower may be present in the inventive formulation at a concentration ranging from about 5 to about 20 weight percent. Preferably, the concentration of German chamomile flower is about 12.5 weight percent.

Fenugreek seed (*trigonelia foenum-graecum*) is a well-known herb used as an anti-inflammatory and anti-spasmodic compound. Fenugreek seed may be present in the inventive formulation at a concentration ranging from about 2 to about 15 weight percent. Preferably, the concentration of fenugreek seed is about 6.2 weight percent.

Fennel seed (*foeniculum vulgare*) is a well-known herb which acts to prevent gas and upset stomach, inhibit spasms in smooth muscles, and reduce pain and fever. Fennel seed may be present in the inventive formulation at a concentration ranging from about 2 to about 15 weight percent. Preferably, the concentration of fennel seed is about 6.2 weight percent.

Skullcap herb (*sculellaria lateriflora*) is a well-known herb used as a sedative and antispasmodic agent. Skullcap herb may be present in the inventive formulation at a concentration ranging from about 2 to about 15 weight percent. Preferably, the concentration of skullcap herb is about 6.2 weight percent.

Cranberry fruit (*vaccinium macrocarpon*) is a well-known herb which acts as an astringent to tone and restrict tissue mucosal discharges. Cranberry fruit may be present in the inventive formulation at a concentration ranging from about 1 to about 8 weight percent. Preferably, the concentration of cranberry fruit is about 3.2 weight percent.

Peppermint leaf (*menthe piperita*) is a well-known herb used to treat gas and indigestion and to ease intestinal cramping. Peppermint leaf may be present in the inventive formulation at a concentration ranging from about 1 to about 8 weight percent. Preferably, the concentration of peppermint leaf is about 3.2 weight percent.

The inventive formulation also comprises a mixture of traditional Chinese herbs. The combination of these Chinese herbs with Western herbs uniquely provides a formulation that sooths the colon, normalizes stool formation, and supports the normal functioning of the bowel. The mixture of Chinese herbs comprises atractylodes root (bai zhu), capillary artemisia herb (yin chen hao), codonopsis root (dang shen), Job's tears seed (yi yi ren), schisandra fruit (wu wei zi), agastache whole plant (huo xiang), Chinese licorice root (zhi gan cao), Chinese thoroughwax (chai hu), ginger root (pao jiang), Korean ash branches bark (gin pi), magnolia bark (hou po), phellodendron bark (huang bai), poria cocos root (fu ling), psyllium seed (che gian zi), Chinese goldthread (huang lian), Chinese white peony root (bai shao), costus root (mu xiang), silver root (fang feng), tangerine peel (chen pi), and angelica root (bai zhi). The concentration of each of these Chinese herbs, as a percentage of the total weight of the mixture of Chinese herbs, may individually range from about 1 weight percent to about 20 weight percent. The mixture of Chinese herbs, as a percentage of the total weight of the inventive herbal formulation, may be present at a concentrations ranging from about 25 weight percent to about 60 weight percent. Preferably, the concentration of the mixture of Chinese herbs is about 37.5 weight percent.

Finally, methylsulfonylmethane, a well-known naturally organic sulfur compound present in the tissues of all plants, animals, and humans, is present in the inventive herbal formulation. The methylsulfonylmethane may be present at a concentration ranging from about 5 weight percent to about 20 weight percent. Preferably, the concentration of methylsulfonylmethane is about 12.5 weight percent.

The aforementioned ingredients may be dried, ground, and mixed together by conventional techniques. Thereafter, the powder mixture may be pressed into tablets or placed in gelatin capsules for oral administration. The inventive herbal formulation may also contain conventional food supplement fillers and extenders such as, for example, rice flour. Conveniently, the inventive herbal formulation may be taken orally at a dosage rate ranging from about 200 to about 2,500 milligrams per day. Preferably, the dosage rate, effective as a food supplement and an intestinal bowel soother, ranges from about 1,400 milligrams per day to about 1,800 milligrams per day.

This invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. An herbal formulation which acts as an intestinal bowel soother, comprising effective amounts of:
    slippery elm bark;
    German chamomile flower;
    fenugreek seed;
    fennel seed;
    skullcap herb;
    cranberry fruit;
    peppermint leaf;
    a mixture of Chinese herbs comprising atractylodes root, capillary artemisia herb, codonopsis root, Job's tears seed, schisandra fruit, agastache whole plant, Chinese licorice root, Chinese thoroughwax, ginger root, Korean ash branches bark, magnolia bark, phellodendron bark, poria cocos root, psyllium seed, Chinese goldthread, Chinese white peony root, costus root, silver root, tangerine peel, and angelica root; and methylsulfonylmethane.

2. The herbal formulation according to claim 1, wherein the concentration of slippery elm bark ranges from about 5 weight percent to about 20 weight percent of the formulation.

3. The herbal formulation according to claim 2, wherein the concentration of slippery elm bark is about 12.5 weight percent.

4. The herbal formulation according to claim 1, wherein the concentration of German chamomile flower ranges from about 5 weight percent to about 20 weight percent of the formulation.

5. The herbal formulation according to claim 4, wherein the concentration of German chamomile flower is about 12.5 weight percent.

6. The herbal formulation according to claim 1, wherein the concentration of fenugreek seed ranges from about 2 weight percent to about 15 weight percent of the formulation.

7. The herbal formulation according to claim 6, wherein the concentration of fenugreek seed is about 6.2 weight percent.

8. The herbal formulation according to claim 1, wherein the concentration of fennel seed ranges from about 2 weight percent to about 15 weight percent of the formulation.

9. The herbal formulation according to claim 8, wherein the concentration of fennel seed is about 6.2 weight percent.

10. The herbal formulation according to claim 1, wherein the concentration of skullcap herb ranges from about 2 weight percent to about 15 weight percent of the formulation.

11. The herbal formulation according to claim 10, wherein the concentration of skullcap herb is about 6.2 weight percent.

12. The herbal formulation according to claim 1, wherein the concentration of cranberry fruit ranges from about 1 weight percent to about 8 weight percent of the formulation.

13. The herbal formulation according to claim 12, wherein the concentration of cranberry fruit is about 3.2 weight percent.

14. The herbal formulation according to claim 1, wherein the concentration of peppermint leaf ranges from about 1 weight percent to about 8 weight percent of the formulation.

15. The herbal formulation according to claim 14, wherein the concentration of peppermint leaf is about 3.2 weight percent.

16. The herbal formulation according to claim 1, wherein the concentration of the mixture of Chinese herbs ranges from about 25 weight percent to about 60 weight percent of the formulation.

17. The herbal formulation according to claim 16, wherein the concentration of the mixture of Chinese herbs is about 37.5 weight percent.

18. The herbal formulation according to claim 1, 16, or 17, wherein the concentration of each of the Chinese herbs, as a percentage of the total weight of the mixture of Chinese herbs, individually ranges from about 1 weight percent to about 20 weight percent.

19. The herbal formulation according to claim 1, wherein the concentration of methylsulfonylmethane ranges from about 5 weight percent to about 20 weight percent of the formulation.

20. The herbal formulation according to claim 19, wherein the concentration of methylsulfonylmethane is about 12.5 weight percent.

21. An herbal formulation which acts as an intestinal bowel soother, comprising:
    from about 5 weight percent to about 20 weight percent slippery elm bark;
    from about 5 weight percent to about 20 weight percent German chamomile flower;
    from about 2 weight percent to about 15 weight percent fenugreek seed;
    from about 2 weight percent to about 15 weight percent fennel seed;

from about 2 weight percent to about 15 weight percent skullcap herb;

from about 1 weight percent to about 8 weight percent cranberry fruit;

from about 1 weight percent to about 8 weight percent peppermint leaf;

from about 25 weight percent to about 60 weight percent a mixture of Chinese herbs comprising atractylodes root, capillary artemisia herb, codonopsis root, Job's tears seed, schisandra fruit, agastache whole plant, Chinese licorice root, Chinese thoroughwax, ginger root, Korean ash branches bark, magnolia bark, phellodendron bark, poria cocos root, psyllium seed, Chinese goldthread, Chinese white peony root, costus root, silver root, tangerine peel, and angelica root; and from about 5 weight percent to about 20 weight percent methylsulfonylmethane.

22. The herbal formulation according to claim 21, wherein the concentration of slippery elm bark is about 12.5 weight percent.

23. The herbal formulation according to claim 21, wherein the concentration of German chamomile flower is about 12.5 weight percent.

24. The herbal formulation according to claim 21, wherein the concentration of fenugreek seed is about 6.2 weight percent.

25. The herbal formulation according to claim 21, wherein the concentration of fennel seed is about 6.2 weight percent.

26. The herbal formulation according to claim 21, wherein the concentration of skullcap herb is about 6.2 weight percent.

27. The herbal formulation according to claim 21, wherein the concentration of cranberry fruit is about 3.2 weight percent.

28. The herbal formulation according to claim 21, wherein the concentration of peppermint leaf is about 3.2 weight percent.

29. The herbal formulation according to claim 21, wherein the concentration of the mixture of Chinese herbs is about 37.5 weight percent.

30. The herbal formulation according to claim 21 or 29, wherein the concentration of each of the Chinese herbs, as a percentage of the total weight of the mixture of Chinese herbs, individually ranges from about 1 weight percent to about 20 weight percent.

31. The herbal formulation according to claim 21, wherein the concentration of methylsulfonylmethane is about 12.5 weight percent.

32. An herbal formulation which acts as an intestinal bowel soother, comprising:

about 12.5 weight percent slippery elm bark;

about 12.5 weight percent German chamomile flower;

about 6.2 weight percent fenugreek seed;

about 6.2 weight percent fennel seed;

about 6.2 weight percent skullcap herb;

about 3.2 weight percent cranberry fruit;

about 3.2 weight percent peppermint leaf;

about 37.5 weight percent a mixture of Chinese herbs comprising atractylodes root, capillary artemisia herb, codonopsis root, Job's tears seed, schisandra fruit, agastache whole plant, Chinese licorice root, Chinese thoroughwax, ginger root, Korean ash branches bark, magnolia bark, phellodendron bark, poria cocos root, psyllium seed, Chinese goldthread, Chinese white peony root, costus root, silver root, tangerine peel, and angelica root; and about 12.5 weight percent methylsulfonylmethane.

33. The herbal formulation according to claim 32, wherein the concentration of each of the Chinese herbs, as a percentage of the total weight of the mixture of Chinese herbs, individually ranges from about 1 weight percent to about 20 weight percent.

* * * * *